(12) United States Patent
Lee

(10) Patent No.: US 10,505,078 B2
(45) Date of Patent: Dec. 10, 2019

(54) METHODS AND APPARATUS FOR ILLUMINATING GEMSTONES

(71) Applicant: Daniel Seeng Keat Lee, Selangor (MY)

(72) Inventor: Daniel Seeng Keat Lee, Selangor (MY)

(73) Assignee: Effulgent Inc., Daly City, CA (US)

( * ) Notice: Subject to any disclaimer, the term of this patent is extended or adjusted under 35 U.S.C. 154(b) by 50 days.

(21) Appl. No.: 15/645,071

(22) Filed: Jul. 10, 2017

(65) Prior Publication Data

US 2018/0033919 A1 Feb. 1, 2018

Related U.S. Application Data

(60) Provisional application No. 62/360,182, filed on Jul. 8, 2016.

(51) Int. Cl.
| | |
|---|---|
| *H01L 29/08* | (2006.01) |
| *H01L 33/46* | (2010.01) |
| *H01L 33/54* | (2010.01) |
| *H01L 51/52* | (2006.01) |
| *H01L 33/58* | (2010.01) |
| *H01L 33/64* | (2010.01) |
| *F21V 33/00* | (2006.01) |
| *G01N 21/87* | (2006.01) |
| *H01L 33/60* | (2010.01) |

(Continued)

(52) U.S. Cl.
CPC .............. *H01L 33/46* (2013.01); *F21V 33/00* (2013.01); *G01N 21/87* (2013.01); *H01L 33/54* (2013.01); *H01L 33/58* (2013.01); *H01L 33/60* (2013.01); *H01L 33/641* (2013.01); *H01L 51/5203* (2013.01); *A44C 15/0015* (2013.01); *A44C 17/02* (2013.01); *F21V 5/06* (2013.01); *F21V 33/0008* (2013.01); *F21W 2121/06* (2013.01); *F21Y 2115/10* (2016.08); *H01L 2224/48091* (2013.01); *H01L 2224/48137* (2013.01)

(58) Field of Classification Search
USPC .......................................................... 257/40
See application file for complete search history.

(56) References Cited

U.S. PATENT DOCUMENTS

| | | | | |
|---|---|---|---|---|
| 6,433,483 | B1 * | 8/2002 | Michael ............. | A44C 15/0015 315/200 A |
| 6,833,539 | B1 * | 12/2004 | Maeda ............... | A44C 15/0015 250/214 AL |

(Continued)

*Primary Examiner* — Caleb E Henry
(74) *Attorney, Agent, or Firm* — Ariel S. Bentolila; Bay Area IP Group, LLC

(57) ABSTRACT

A light source comprising a substrate, wherein the substrate is coated with a transflective thin film optical coating, wherein the coating results in a metallic mirror and/or iridescent effect on the substrate; and a light emitting diode comprising an internal circuitry, wherein when the light source in a switched-Off mode the metallic mirror effect or the iridescent effect conceal internal circuitry of the light emitting diode to provide an aesthetic look and color on the gemstone, wherein when the light source is switched-ON the transflective thin film allows LED light to transmit through the substrate, wherein the light source comprises a substantially invisible light source integrated onto a substrate. In other embodiments, LED may include OLED, transparent inorganic LED, flexible COF LED, etc. . . . . In embodiments, the gemstone may be foiled, unfoiled, multi-facetted, colorless, colored, etc. . . . .

19 Claims, 12 Drawing Sheets

(51) Int. Cl.
  *A44C 15/00*    (2006.01)
  *F21V 5/06*     (2006.01)
  *F21W 121/06*   (2006.01)
  *F21Y 115/10*   (2016.01)
  *A44C 17/02*    (2006.01)

(56) References Cited

U.S. PATENT DOCUMENTS

| | | | | |
|---|---|---|---|---|
| 9,635,912 | B1* | 5/2017 | Chen | H02J 7/0063 |
| 2004/0164292 | A1* | 8/2004 | Tung | G02F 1/133603 |
| | | | | 257/40 |
| 2006/0059947 | A1* | 3/2006 | Gore | A44C 5/00 |
| | | | | 63/1.13 |
| 2007/0018943 | A1* | 1/2007 | Bayrle | G02F 1/133555 |
| | | | | 345/102 |
| 2009/0103161 | A1* | 4/2009 | Kothari | G02F 1/13306 |
| | | | | 359/245 |
| 2011/0084303 | A1* | 4/2011 | Cho | H05K 1/0203 |
| | | | | 257/99 |
| 2011/0128212 | A1* | 6/2011 | Kothari | G02B 26/001 |
| | | | | 345/82 |
| 2012/0127140 | A1* | 5/2012 | Ryan | G09G 3/3648 |
| | | | | 345/207 |
| 2014/0035836 | A1* | 2/2014 | Cui | G06F 3/0421 |
| | | | | 345/173 |
| 2014/0184573 | A1* | 7/2014 | Nemchuk | G02B 26/0833 |
| | | | | 345/204 |
| 2015/0009654 | A1* | 1/2015 | Chan | H05B 33/086 |
| | | | | 362/104 |
| 2015/0311470 | A1* | 10/2015 | Guimard | C03C 17/3644 |
| | | | | 257/40 |

* cited by examiner

Crystal LED on flexible printed circuit
– LED/LED driver dies are invisible due to the AB effect

METHODS AND APPARATUS FOR ILLUMINATING GEMSTONES

CROSS-REFERENCE TO RELATED APPLICATIONS

The present Utility patent application claims priority benefit of the U.S. provisional application for patent Ser. 62/360,182 Entitled METHODS & APPARATUS FOR ILLUMINATING TRANSFLECTIVE GEMSTONES" filed 8 Jul. 2016 under 35 U.S.C. 119(e). The contents of this related provisional application are incorporated herein by reference for all purposes to the extent that such subject matter is not inconsistent herewith or limiting hereof.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to illuminated gemstones. More particularly, certain embodiments of the invention relate to methods and apparatus for fabricating transflective gemstones and LED.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Gemstones, by nature, synthetic or imitated, precious, semi-precious stones, cut glass crystals are integrated onto a variety of substrates, for example, apparels, shoes, jewelries, bags, and other accessories to enhance the beauty of these substrates with their color and sparkling beauty. Gemstones/crystals can refract light for sparkling beauty reason but do not have light source and cannot control the light to provide indication, text, images and video to communicate based on many factors such as where, when, why, how and what light color. For example, the gemstones LED combined with a CPU and GPS can light up the gemstone to show a person is within a specific location, or combined a CPU and clock to show alarm clock ringing or combined with phone to show incoming call alert. The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that typical gemstone/crystal and LED combination lighting devices known today appear to exhibit the visual aspects of the LED when switched-ON and expose the internal circuitry when switched-OFF. In applications where visual aspect is important in switched-ON and switched-OFF states, the exposure of the internal circuitry when viewed in close-up may be considered non-aesthetic, for example, in wearable smart jewelry, apparels, and mobile computing devices. Further, it is believed that methods to conceal object with metallic light reflection while providing controllable means for exposing objects are known to use transparent one-way mirror coating, i.e., a transflector. The transparent one-way mirror coating may allow light penetration and is typically used to cover LCD display. However, opaque mirror layer commonly known as "foiling" in cut glass crystal doesn't not allow light transmission behind the foiling. To allow light transmission holes may be opened in the foiling or an opaque mirror may be used in the cavity to conceal light source. Imitated gemstone of cut glass crystal typically employed opaque mirror coating a.k.a. "foiling" at the back to enhance ambient light reflection. The coating/foiling may however not allow LED light to shine from the back of the crystal without specific openings made in the foiling as mentioned herein above. Further, integrating LED onto pointed back crystal that mimics the diamond shape set within flexible metal cup chain still appears to be a challenge in the industry and most substrates for mounting the crystals are soft, flexible, bendable leathers, fabrics or fixed curved metal.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF SOME EMBODIMENTS

Figure 1:
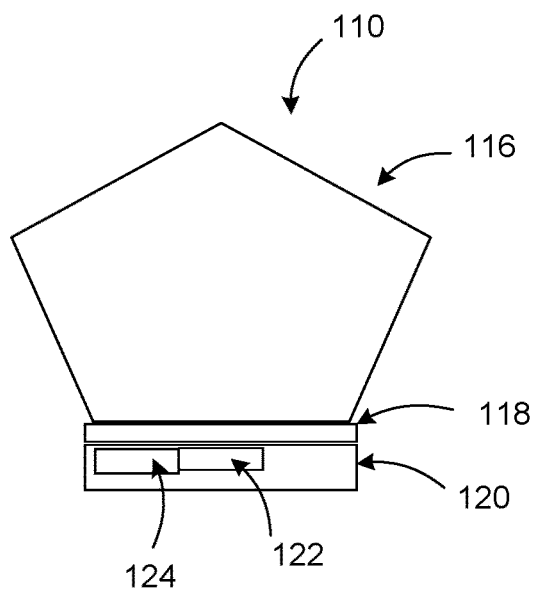
FIG. 1 (a), FIG. 1 (b), and FIG. 1 (c) illustrate an illuminated transflective gemstone-LED combination, in accordance with an embodiment of the present invention, wherein FIG. 1 (a) illustrates a back coated/reversed coating of a gemstone, FIG. 1 (b) illustrates a front coated/surface coating of a gemstone, and FIG. 1 (c) illustrates a fully coated gemstone.
Figure 1:
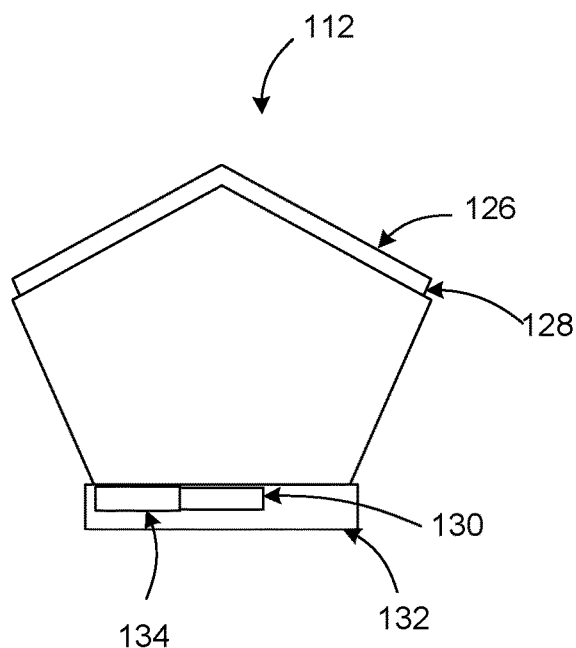
Figure 1:
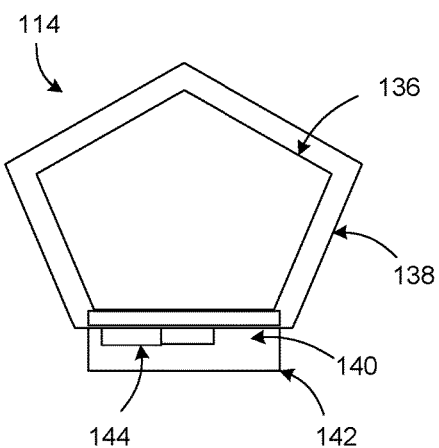

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-insuit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other,"

"close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, in re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of, or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. sctn. 112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of" and "consisting essentially of" where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Embodiments of the invention disclosed herein may provide an illuminated transflective gemstone-LED combination, methods and apparatus for illuminated gemstones. In one exemplary embodiment, the illuminated gemstones may include features including, but not limited to, ambient light reflection and controllable LED light source shining through the gemstone, concealed LED circuitry/transparent LED, and conformable to rigid and/or flexible device. Accordingly, the illuminated gemstones disclosed herein may include transflective gemstones and a controllable LED package, which may be operative in ambient light reflective mode and LED light transmissive mode i.e., provide a substantially invisible light source integrated onto a gemstone. The illuminated gemstones may be able to conceal the LED and may thus provide a seamless gemstone customization. It may be appreciated by a person with ordinary skill in the art, in light of and in accordance with the teachings of the present invention, that crystal LED's available in the industry may be typically based on back lit light source. The backlit light source may be exposed via opening(s) in the foiling or no foiling at all. In various embodiments, the invention disclosed herein may provide designs, methods and apparatus for implementing side lit and front lit light sources. The ability to mimic the ambient light shining from all directions onto crystal may be able create controllable sparkling effect that may also provide information in some embodiments.

Accordingly, embodiments of the invention disclosed herein may provide illuminated gemstones, and methods and apparatus for the illuminated gemstone that may allow ambient light reflection and controllable LED light source shining through the gemstones, concealment of LED circuitry/transparent LED, and conformance to rigid and/or flexible device. In an exemplary embodiment, the invention disclosed herein may include at least one gem stone and at least one LED light source. In certain embodiments, the invention disclose herein may also include a plurality of gemstones, a plurality of LED light sources, form factor and positioning and methods of mirror coating.

It may be appreciated by a person with ordinary skill in the art, in light of and in accordance with the teachings of the present invention, that gemstones may include natural, synthetic or imitated, precious, semi-precious stones, or a combination thereof. For example, gemstones may include stones including, but not limited to, ruby, emerald, sapphire, and the like. In various embodiments, the gemstones may have different physical appearance including but not limited to, transparent or translucent or colored or colorless, having various shapes and facets, and flat back or pointed back. In certain embodiments, the gemstones may include imitation gemstones made of glass. For example, cut-glass crystal; made of polymers, for example, acrylic, polycarbonate; and made of silicone.

It may be appreciated by a person with ordinary skill in the art, in light of and in accordance with the teachings of the present invention, that LED light source may include, but is not limited to, inorganic LED package made with molded casing or wafer level chip select package, thin film flexible inorganic LED made with chip-on-board/chip-on-flex/flip chip-on-flex manufacturing technology, transparent display LED/LCD made with chip-on-board/chip-on-glass technology, and mirror OLED lighting/display that are rigid/flexible, bendable and conformal. In an exemplary embodiment, conventional LED package that is rigid may be used and may be applied on flexible printed circuit or PCB, PET with conductive ink. In another exemplary embodiment, thin film flexible LED, the inorganic LED may be attached/embedded using die-on-flex or chip-on-flex method onto a flexible printed circuit board (FPC) or a conductive ink printed PET/polyimide film. In various embodiments, the LED package or LED chip scale package (CSP) or LED wafer level chip scale package (WLCSP) or LED die may include a single-color LED, a multi-color LED i.e., a red-green-blue (RGB) LED, a red-green-blue-white (RGBW) LED, an LED array, an LED matrix display, and a strings of daisy chained LED. In various embodiments, the LED(s) may be driven by a central processing unit (CPU), a microcontroller, or a LED driver. In various embodiments, the LED (s) may be connected into a matrix LED driver or daisy chained driver such as WS2812B, SK6812, SK6805, APA102, SK9822, and the like.

In various exemplary embodiments, the transflective gemstone-LED combination described herein provide at least four methods of coating on a gemstone/crystal and a plurality of coated materials for use as the transflective gemstones. In one embodiment, the first method of mirror coating may include a transflector coating. The transflector coating may include a one-way mirror coating or iridescent dichroic mirror coating. In one embodiment, the second method of mirror coating may include an opaque/a non-transparent/standard mirror coating. In one embodiment, the third method may include no mirror coating. In one embodiment, the fourth method may include a transflector which may be a switchable mirror i.e., a reversible electrochemical mirror, operating in two states, that is in mirror state when power is switched-OFF and in transparent state when power is switched-ON.

As mentioned hereinabove, the first method includes a transflector coating. The transflector coating may include a reflective thin film optical mirror coating which may provide a one-way mirror or iridescent dichroic mirror that may operate in a reflective mode i.e., a mirror state in ambient light by reflecting light and surrounding images, i.e., provide a mirror effect, when the light source or LED is in a switched-off mode. The mirror may operate in a transmissive mode by allowing light penetration when the light source or LED is in a switched-on mode. In a reflective mode, when the light source or LED is switched-off, the mirror effect may assist in concealing internal LED circuitry. In a transmissive mode or transparent state the mirror in a transmissive mode may assist in allowing LED light penetration during which the light source or LED is switched-on. Both one way mirror and dichroic mirror share the same transflective nature, however, there is a difference between the two. The one way mirror is a standard beam splitters which split incident light (transmit and reflect light) by a specified ratio that is independent of wavelength or polarization state. The dichroic mirror split light (transmit and reflect light) by wavelength thereby making colored mirror.

In one exemplary embodiment, the one-way mirror coating may be provided on the back of the gemstone to replace the opaque mirror foiling (typically present in mirrors to provide the reflective effect). In one exemplary embodiment, the iridescent dichroic mirror coating may be provided on the surface of the gemstone. It may be appreciated by a person with ordinary skill in the art, in light of and in accordance with the teachings of the present invention, that the iridescent effect may be similar to thin-walled soap bubbles or very thin oil film that provides a rainbow color effect. This effect is due to the interference of light ray in thin-film optics. It may be appreciated by a person with ordinary skill in the art, in light of and in accordance with the teachings of the present invention, that interference colors can only appear in extremely thin films which are of a thickness comparable to one fourth the wave length of light and which are at least partially transparent. It may be appreciated by a person with ordinary skill in the art, in light of and in accordance with the teachings of the present invention, that depositing reflective coating of various materials in extremely thin films which are still partially or considerably transparent, can secure a wide range of colored mirrors of various characteristics for various rays of light to realize iridescent. For example, methods used to produce products such as carnival glass, rainbow glass, aurora glass, dichroic glass and dichroic glass jewelry i.e., 'Iridill' by Fenton in 1908, 'Aurora Borealis' effect (AB) by Swarovski in 1955, and PVD-coated dichoroic glass. Although dichroic technically means displaying two different colors by undergoing a color change in certain lighting conditions, the commercial title of "dichroic" can also display three or more colors (trichroic or pleochroic) and even iridescence.

It may be appreciated by a person with ordinary skill in the art, in light of and in accordance with the teachings of the present invention, that the facets on the gemstone/rhinestone provide different view angles and hence different color facets as understood in goniochromism. Typically, most crystals may be foiled. The AB coated crystals may sometimes be unfoiled to allow for light from the back of the crystal to create more light interference and colors. In embodiments, when an AB coated flat back crystal back is shielded off from light when placed on a dark surface, the metallic surface coating may become more pronounced, like a gold mirror reflection. In embodiments, when an AB coated flat back crystal back is placed on a white bright surface, some facets of the AB coated crystal may appear like a transparent color gemstone. Gemstone with steeper facets cut such as Swarovski 2088 will exhibit more mirror effect on a bright background than a chessboard Swarovski 2035.

In an exemplary embodiment, the thin film optical coating i.e., the one-way mirror coating or iridescent dichroic mirror coating described above may be applied onto the gemstones, including but not limited to imitation gemstones, for example, cut-glass crystals. In one embodiment, the resultants coated crystal may be an unfoiled crystal, vacuum coated with thin film metal including, but not limited to, gold, silver, aluminum, metal oxide, and alloys that may allow light to pass through when the LED is switched-ON and appear as a mirror when the LED is switched-off.

It may be appreciated by a person with ordinary skill in the art, in light of and in accordance with the teachings of the present invention, that there are various methods known for coating. In various embodiments, the coating process may be carried out by vacuum sputtering, vapor coating (physical vapor deposition or chemical vapor deposition), spray coating, syringe coating, spin coating, drop coating, and the like. The one-way mirror coating may have a controlled visible light transmittance based on a thickness of the metal layer being coated. It may be appreciated by a person with ordinary skill in the art, in light of and in accordance with the teachings of the present invention, that a low visible light transmittance may have a stronger mirror reflective effect but more diffused/lesser light transmission for LED light source. A dichroic coating may include multi-layer coating having same or different refractive indices. As mentioned hereinabove, when the light source is switched-OFF, the mirror effect may be used to conceal the internal LED chip, LED driver, wire bonding, yellow phosphorus encapsulant and/or other semiconductor chips. In an exemplary embodiment, the coating material may include a material having a melting point of greater than or equal to above 240 degrees Celsius and of lead free surface mount technology reflow temperature, to ensure that during the SMT process the coating may not melt and smear away.

Referring to FIG. 1 (*a*), FIG. 1 (*b*), and FIG. 1 (*c*), is illustrated exemplary gemstone/crystal coatings used in a method of light enhancement in an illuminated transflective gemstone-LED combination in accordance with an embodiment of the present invention. FIG. 1 illustrates gemstones/crystals coated in at least three different manners. FIG. 1(*a*) 110 illustrates a back coated/reversed coating of a gemstone. FIG. 1(*b*) 112 illustrates a front coated/surface coating of a gemstone. FIG. 1 (*c*) 114 illustrates a fully coated gemstone. FIG. 1 (*a*) 110 shows a gemstone 116, a dichroic mirror coating 118 on the back of the crystal, an LED die 120 at the back of the gemstone i.e., a back lit gemstone; a flexible circuit 122, and an optional LED driver 124. FIG. 1 (*b*) 112 shows a gemstone 126, a dichroic mirror coating 128 on the front of the crystal, an LED die 130 at the back of the gemstone i.e., a back lit gemstone; a flexible circuit 132, and an optional LED driver 134. FIG. 1 (*c*) 114 shows a gemstone 136, a dichroic mirror coating 138 on all sides of the crystal i.e., fully coated crystal, an LED die 140 at the back of the gemstone i.e., a back lit gemstone; a flexible circuit 142, and an optional LED driver 144. In the exemplary embodiment described in FIG. 1, in all FIG. 1(*a*), FIG. 1 (*b*), and FIG. 1 (*c*), the LED die and LED driver die may be embedded onto FPC using COF (chip-on-flex) and the light sources includes a back lit LED light source.

Figure 2:
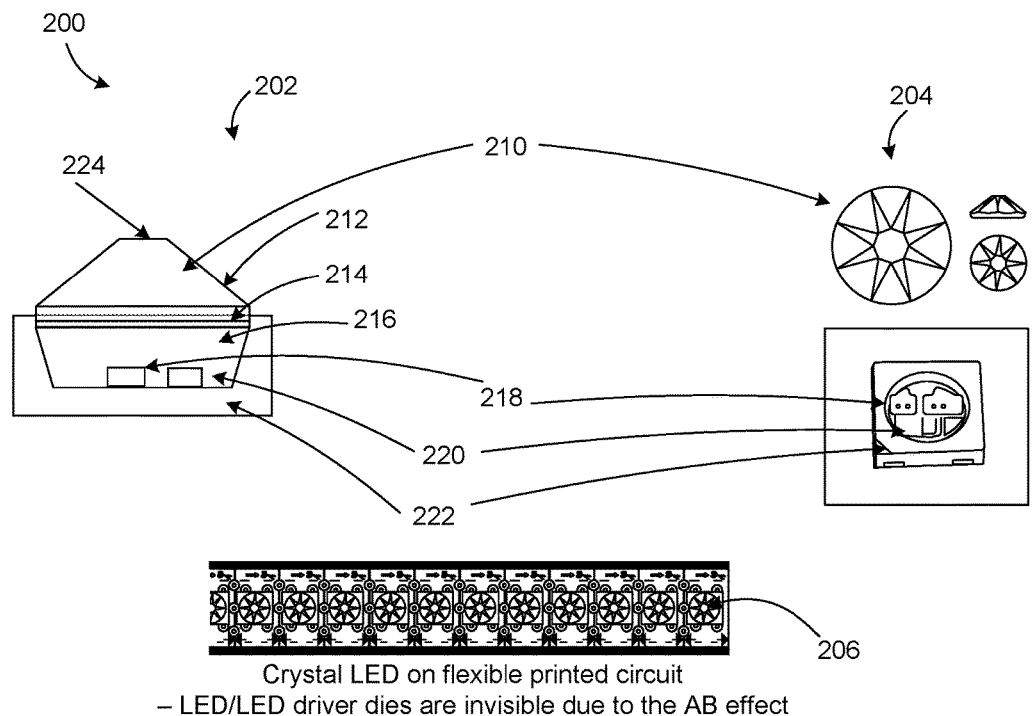
FIG. 2 illustrates an illuminated transflective gemstone-LED combination, in accordance with an embodiment of the present invention.

Referring to FIG. 2, is illustrated an illuminated transflective gemstone-LED combination, in accordance with an embodiment of the present invention. FIG. 2 illustrates an integrated driver LED SMD package of SK6812 mounted with gemstone Swarovski 2088 Xirius unfoiled AB coated flat back on top. The gemstone diameter is slightly smaller (e.g., 0.1 millimeter smaller) than the LED conical cavity opening diameter. The LED package is SMT mounted on FPC. Without the gemstone, the SMD LED package shows exposed LED dies and driver which is not aesthetic for close-up jewelry use. With the gemstone mounted, the dichroic mirror sheen may hide the internal LED circuitry. As shown in view 202 of FIG. 2, the illuminated transflective gemstone-LED combination 200 may include an unfoiled flat back crystal 210, the crystal 210 having a surface Aurore Boreale effect 212 (gold vacuum coated Swarovski Aurore Boreale effect as a front coating of Swarovski flat back rhinestone crystal 2088), a clear adhesive 214, a clear silicone encapsulate 216, a RGB LED die 218, an LED driver 220, and an LED package 222. Pictorial view 204 shows the include an unfoiled flat back crystal 210, the RGB LED die 218, the LED driver 220, and the LED package 222 and the ambient light reflection through the crystal 224. In view 206, is shown a plurality of crystal-LED combinations on a flexible printed circuit, where the LED and the LED driver dies may be invisible due to the Aurore Boreale effect. Accordingly, in an exemplary embodiment, FIG. 2, illustrates an integrated driver LED surface mounted devices (SMD) package of SK6812 mounted with gemstone Swarovski 2088 Xirius unfoiled AB coated on top side with a flat back, as show in FIG. 1 (*b*) 112. In the embodiment, described in FIG. 2, the LED 218 is positioned as a back lit to the crystal 210. In one embodiment, the mounting of gemstone, for example, Swarovski 2088 a flat back rhinestone which sometimes may be known to have a wide size tolerance, the cavity in the LED package may be designed to be conical and the gemstone diameter is usually 0.1 mm smaller than the top opening diameter of the cavity. This lock-in mechanism may protect the gemstone from movement as panels of LEDs are transferred around to heat/UV curing process. The LED package may include a surface-mount technology (SMT) mounted on FPC. As described hereinabove, with the gemstone mounted, the dichroic mirror sheen hides the internal LED circuitry and may provide the required aesthetics for us in jewelry where close up aesthetics may be required.

In one embodiment, the gemstone/crystal may be mounted onto the LED by using a pick and place machine using a clear adhesive 214 to hold the gemstone in place, as shown in FIG. 2. Examples of the clear adhesive may include, but may not be limited to, acrylic, epoxy, or silicone based adhesives cured by UV, thermal, or at room temperature, for example, UV glue AA349 manufactured by Henkel and silicone glue 3145 RTV manufactured by Dow Corning. It may be appreciated by a person with ordinary skill in the art, in light of and in accordance with the teachings of the present invention, that the type and amount of adhesive used to mount the gemstone may be sufficient for the gemstone to be held in place for a sufficient period of time and may be dependent on the LED and the crystal sizes.

In an exemplary embodiment, the mounting of the gemstone may be done after the LED package is mounted onto the PCB or FPC via a lead free SMT process as described hereinabove. In certain embodiments, the clear adhesive 214 may not withstand lead free high temperature process and hence a post SMT (surface mount technology) process may be employed. In another embodiment, a high temperature tolerant bond may be achieved by replacing the LED encapsulant 216, for example, with a clear silicone encapsulant, within the cavity of LED package 222 with an another encapsulant that may have high clarity and adhesive property, for example, silicone LED encapsulate OE6370 manufactured by Dow Corning. After the encapsulant is injected via a jet dispenser into the cavity in the LED package, the gemstone may then be mounted onto the package. The process may be followed by a curing procedure depending on what adhesive is used for fixing the gemstone onto the package. A standard baking/heat curing procedure of about 150 degrees Celsius for a period of about four to six hours may be employed where the adhesive requires heat curing. UV curing may be employed for adhesives that require UV curing. The gemstone/crystal-LED combination may be able to sustain short periods of lead free high temperature SMT process. The pre-SMT process for gemstone mounting method may provide more freedom of design to designers to mount the component onto a variety of PCB/FPC designed by themselves while the post-SMT process for gemstone mounting method may require a manufacturer to have a precise glue dispenser and UV light in addition to a standard SMT assembly line.

It may be appreciated by a person with ordinary skill in the art, in light of and in accordance with the teachings of the present invention, that in certain embodiments, the gemstone/crystal may be mounted without adhesive. In this embodiment, the mounting may be achieved using methods including, but not limited to, metal cup chain, bezel, prong setting that holds the crystal onto LED (not shown in figure), and the like.

Figure 3:
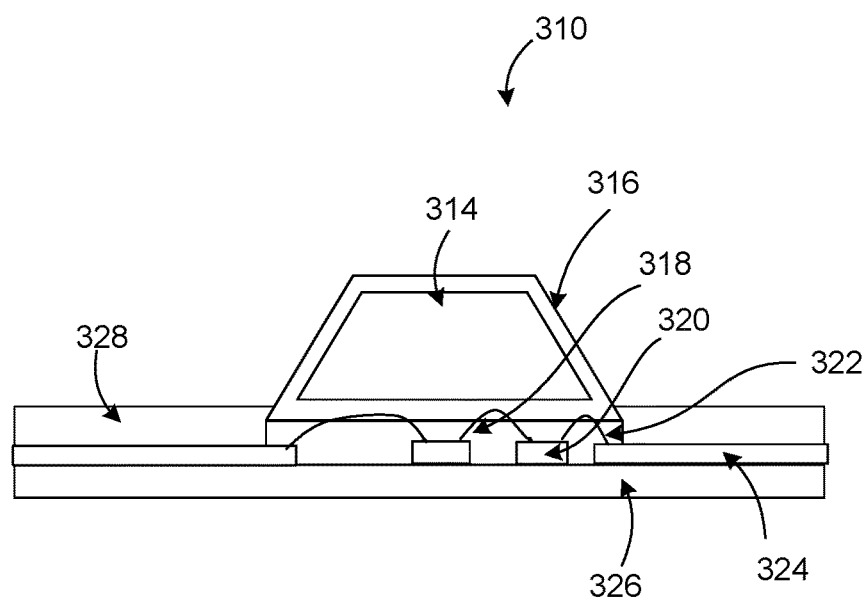
FIG. 3 (a), and FIG. 3 (b) illustrate a cross-sectional view and a top view of an illuminated transflective gemstone-LED combination, in accordance with an embodiment of the present invention.
Figure 3:
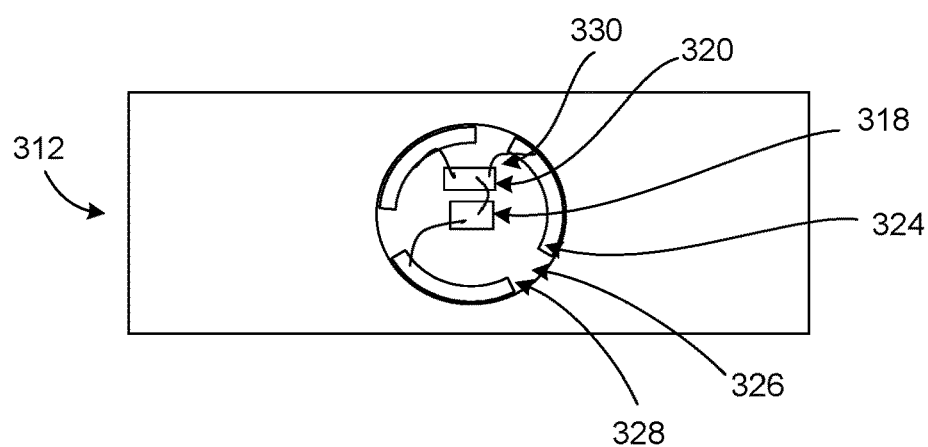

Referring to FIG. 3 (*a*), and FIG. 3 (*b*) is illustrated a side cross-sectional view 310 and a top cross-sectional view of an illuminated transflective gemstone-LED combination, in accordance with an embodiment of the present invention. FIG. 3(*a*) 310 illustrates a front cross-sectional view of an unfoiled gemstone with dichroic mirror coating mounted on COF thin film LEDs. In FIG. 3(a) shows the illuminated transflective gemstone-LED combination to include an unfoiled crystal 314, dichroic mirror coatings 316 (with various options possible as described with reference to FIG. 1), LED die 318—back lit in this embodiment, LED driver 320 (optional in certain embodiments), clear encapsulant with adhesive properties 322, for example, Dow Corning OE6370, copper conductor 324, polyimide 326, and coverlay 328, for example, Dupont Pyralux HXC black coverlay—black in one embodiment. It may be appreciated by a person with ordinary skill in the art, in light of and in accordance with the teachings of the present invention, that the copper conductor 324 may include copper in flexible printed circuit board in one embodiment. In certain embodiments, the conductor may include, but is not limited to, nano silver ink on PET and the LED is flip chip LED.

FIG. 3(b) 312 illustrates a top cross-sectional view of an unfoiled gemstone with dichroic mirror coating mounted on COF thin film LEDs with wire bond COF LED FPC with LED dies and driver and shows how the coverlay and polyimide construct an LED opening shape much like LED package opening. FIG. 3(b) shows the illuminated transflective gemstone-LED combination to include a wire bond 330 (optional in certain embodiments), the led driver 320 (optional in certain embodiments), the LED die 318 (back lit in certain embodiments), the copper conductor 324, polyimide layer 326, and the coverlay 328—black in one embodiment.

In one embodiment, a 360 degree light output may be realized, by using a flexible glass in place of polyimide 326, an ITO transparent trace in place of the copper conductor 243 and a clear coverlay/film 328. The LED die 318 may be mounted using chip-on-glass (COG) technology wherein it may be glued with anisotropic conductive film adhesive onto a conductor made of transparent conductive ink such as ITO or polymer or graphene or metallic nanowire.

In one embodiment, the LED shown in FIG. 3, the LED may be thin film LED and may comprise of COF/FCOF/wirebond LED dies 318 and LED driver 320, including a passive component such as a capacitor (not shown in figure) disposed on an FPC.

It may be appreciated by a person with ordinary skill in the art, in light of and in accordance with the teachings of the present invention, that with advances in technology silicon semiconductors used in LEDs may continue to shrink in size and thickness. Moreover, above about a thickness of about 50 nanometers, silicon may be rigid and brittle, while below a thickness of about 50 nanometers, ultra thin silicon may be flexible and strong as stainless steel. Further, below a thickness of about 10 nanometers, ultra-thin silicon die may be transparent and very flexible. Accordingly, the LED die 318 may be near invisible and flexible and suitable for roll-to-roll processing. The FPC may be a single layer or a multi-layer of copper. Typically, lower number of copper layers may be preferred for bendability. It may be appreciated by a person with ordinary skill in the art, in light of and in accordance with the teachings of the present invention, that the standard polyimide as an LED substrate may usually be translucent yellow and may cause light leakage. As shown in FIG. 3a 310 and FIG. 3b 312, in certain embodiments it may be preferred that the polyimide 326 is opaque white polyimide that can reflect LED light where the LED die reside on via die attach adhesive (not shown). For example, the polyimide 326 is Taimide's white polyimide or top coated white polyimide to reflect the LED light. In other embodiment, polyimide 326 may be normal translucent yellow polyimide laminated with additional black coverlay (not shown) in the FPC most bottom layer to absorb LED light passing through translucent yellow polyimide. In other embodiment, the polyimide 326 below is added with additional copper layer (not shown) such that the copper plane is solid uncut copper plane that is larger than the coverlay LED opening. This opaque copper plane is used to block off the LED light from leaking.

In various embodiments, the coverlay opening may be cut into various shapes, including but not limited to, a circle, a square, a rectangle, and the like shapes to form a single LED pixel using die cut/laser cut with known skill. As mentioned hereinabove, the opening may be slightly larger than the gemstone for the opening to lock-in the gemstone. As described with reference to FIG. 3a 310 above, the cavity stack-up i.e., the depth created by forming a circular opening in the coverlay as shown in FIG. 3b, to mount the LED, LED driver, apply the encapsulant, etc. in the substrate, may consist of the coverlay 328 and copper layer 324 with additional adhesive between layers (not shown) and should be deep enough for the LED die 318, the LED driver 320, the wire bond 330 to reside and the gemstone 314 to sink-in by about 0.1 millimeter. As mentioned above, the coverlay 328 may be preferred to be dark i.e., black in color to enhance the LED opening shape. It may be appreciated by a person with ordinary skill in the art, in light of and in accordance with the teachings of the present invention, that if more LED openings may be needed per crystal, a black mask may be cut in the coverlay or an additional layer of some film as black mask, to form the many openings for more LED per crystal avoiding creating more openings on a foiled crystal. The clear encapsulant made of silicone/epoxy 322 may cover and protect the LED dies and driver. In various embodiments, the gemstone 314 may then be mounted on top of the LED opening either using an adhesive or using metal settings.

It may be appreciated by a person with ordinary skill in the art, in light of and in accordance with the teachings of the present invention, that the assembly of the thin film flexible LED may be automated either in a batch to batch method or a roll to roll processing method. In one embodiment, the method disclosed herein may use the gemstone as a rigid material to function as a solid substrate to hold the LED, LED driver, including other semiconductor such as CPU, memory, MEMS sensors and etc. firmly and protect it much like a molded package and prevent from over bending or stretching since otherwise the flexibility of the FPC may cause bending stress on the LED dies and driver interconnect and may fail at certain bending radius of the FPC. The bending protection may also be provided by including metal cup chain and bezel settings. In stretchable LED FPC design, the gemstone forms the non-stretchable FPC region to protect the semiconductor within and the serpentine shape FPC forms the stretchable FPC region. It may be appreciated by a person with ordinary skill in the art, in light of and in accordance with the teachings of the present invention, that the benefit of thin film LED is more conformal to the crystal shape, for example, a pointed back crystal.

Figure 4:
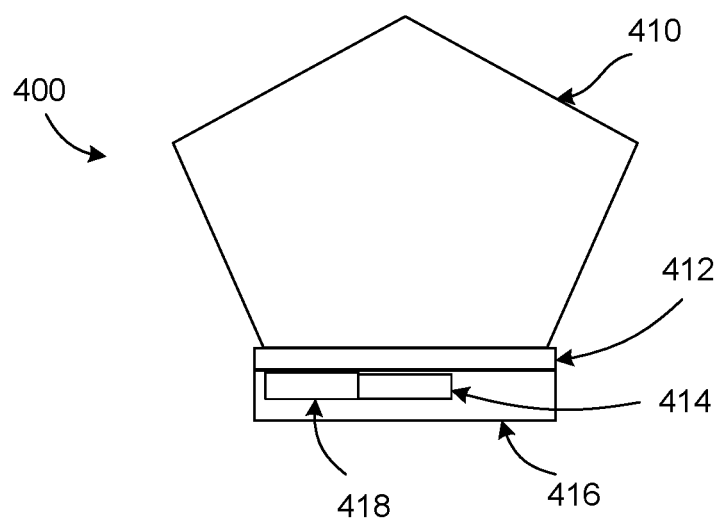
FIG. 4 illustrates an illuminated transflective gemstone-LED combination, in accordance with an embodiment of the present invention.

FIG. 4 illustrates an illuminated transflective gemstone-LED combination, in accordance with an embodiment of the present invention. FIG. 4 illustrates an embodiment with an unfoiled crystal without effect 410, a one-way mirror coating on a transparent film/glass or switchable mirror 412, an LED die 414 (back lit in certain embodiments), a flex circuit 416, and an LED driver 418. In certain embodiments, the crystal may include an effect, for example, a mirror coating.

Figure 5:
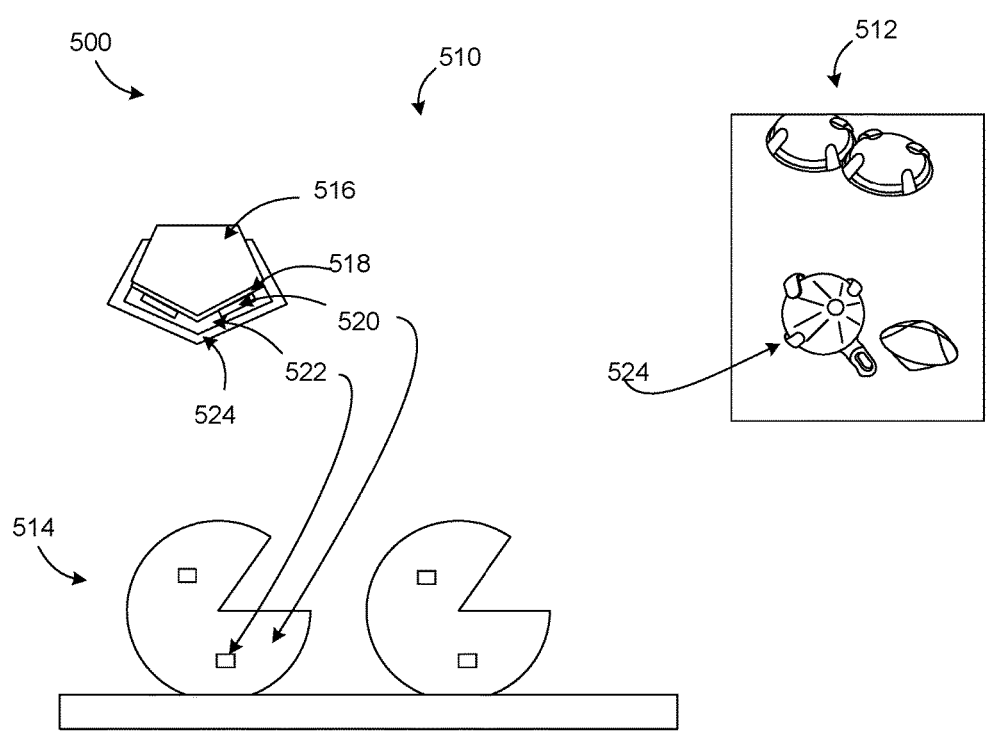
FIG. 5 illustrates an illuminated transflective gemstone-LED combination, in accordance with an embodiment of the present invention.

Referring to FIG. 5 is illustrated an illuminated transflective gemstone-LED combination, in accordance with an embodiment of the present invention. In an exemplary embodiment, FIG. 5 illustrates an embodiment with an unfoiled gemstone with effect and thin film COF LED adapted to a pointed back cup chain. As shown in view 510, the illuminated transflective gemstone-LED combination may include a pointed back unfoiled crystal 516, an effect in the form a one-way mirror coating 518 placed on the pointed portion of the crystal, an LED die 520 (back lit in certain embodiments), a flex circuit 522; and a pointed back cup chain 524. View 512 shows the pointed back cup chains 524 in greater detail.

In one embodiment, referring to FIG. 4 and FIG. 5, the one-way mirror coating 412, 518 may be provided on a transparent rigid material or a transparent flexible film material, for example, including but not limited to rigid/flexible glass; polymers, for example, polycarbonate, acrylic, polyimide, polyester, PET film, and the like. The one-way mirror coating 412, 518 may include a one-way mirror tinted window film in certain embodiments. As mentioned, the gemstone/crystal 410, 516 in this embodiment may be unfoiled and without effect i.e., a one-way mirror coating which is provided separately. The one-way mirror coating material 412, 518 may be sandwiched between the crystal 410, 516 and the LED die 414, 520.

It may be appreciated by a person with ordinary skill in the art, considering and in accordance with the teachings of the present invention, that the one-way mirror coating 412, 518 may be provided using different techniques including but not limited to vacuum coating using a film, vapor, or powder of the coating material.

In one embodiment, the one-way mirror coated film may be transparent and may be integrated onto a thin film die-on-flex LED process since the flexible printed circuit is a process of providing laminated layers of film. Alternatively, it can be adhered onto the opening lens of an LED package. In certain embodiments, a transparent one-way mirror coating may also be coated onto LED lens or the encapsulant made of silicone, polycarbonate or acrylic. In certain embodiments, it may need to be ensured that no air bubble is captured in the process of joining the transparent one-way mirror coating with clear adhesive on mounting the gemstone/crystal and LED. In various embodiments, the LED die may be placed to obtain a front lit or a side lit (edge lit) configuration. In one embodiment, the LED die is placed in a back lit configuration. LED die mounted on a 2D FPC 514 can be rolled up into a cone shape in 3D to be inserted in the pointed back cup chain 524 and then mounted with pointed back unfoiled crystal 516. It may be appreciated by a person with ordinary skill in the art, considering and in accordance with the teachings of the present invention, that 2DFPC 514 is an exemplary illustration of how a 2D FPC may be folded into 3D cone shape to conform to a pointed back crystal. Accordingly, the 2D FPC may be folded to conform to gemstone having various shapes. It may be appreciated by a person with ordinary skill in the art, considering and in accordance with the teachings of the present invention, that as used herein the word "transparent" may refer to a mineral which when coated on a gemstone or crystal may provide a distinct outline of an object viewed through the coated gemstone or crystal; as used herein the word "translucent" may refer to a mineral which when coated on a gemstone or crystal may transmit light through the coated gemstone or crystal but no objects can be seen through it; and as used herein, the word "opaque" may refer to a mineral which when coated on a gemstone or crystal may transmit no light even through the thinnest edges of the coated gemstone or crystal.

Figure 6:
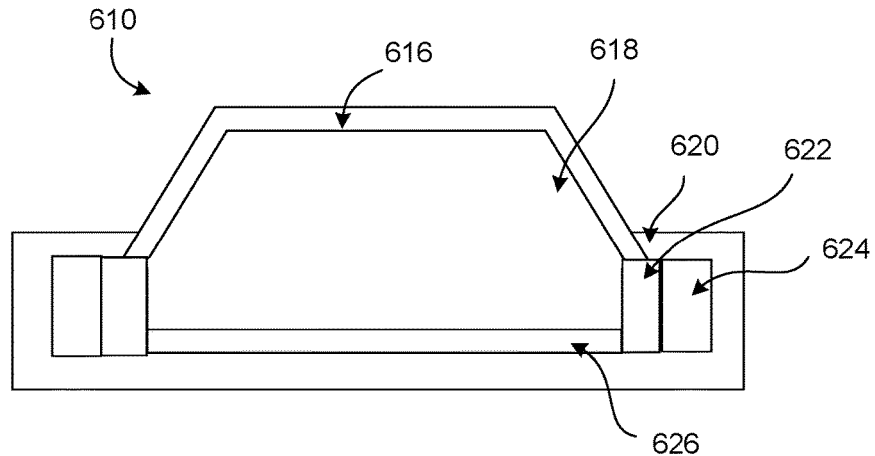
FIG. 6 (a), FIG. 6 (b), and FIG. 6 (c) illustrates an illuminated transflective gemstone-LED combination, in accordance with an embodiment of the present invention.
Figure 6:
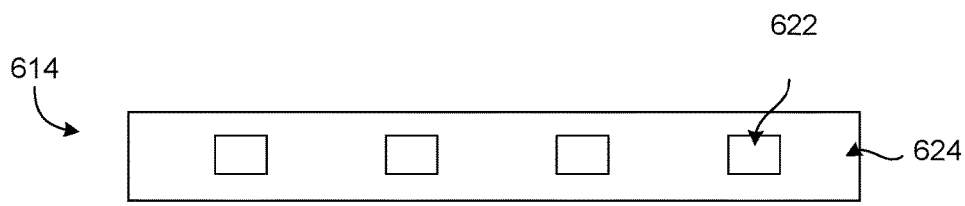
Figure 6:
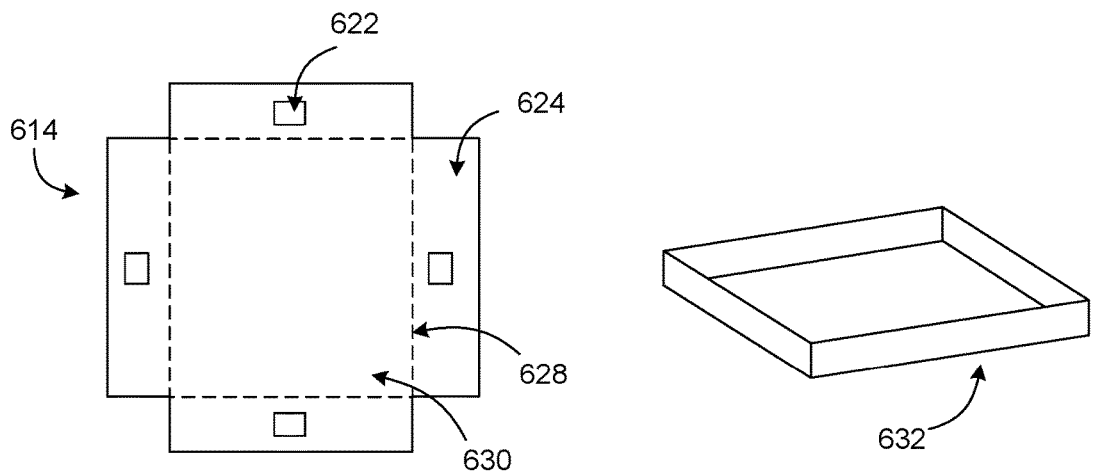

In one embodiment, the second method of mirror coating mentioned hereinabove may include an opaque mirror coating, i.e., a non-transparent standard mirror coating. In one embodiment, the opaque mirror coating may be applied onto the gemstone/crystal and the resultant crystal may be known as a "FOILED" crystal 618, shown in FIG. 6 (a) 610. The crystal 618 may be configured such that the LED light cannot penetrate through from the back of the foiling. It may be appreciated by a person with ordinary skill in the art, in light of and in accordance with the teachings of the present invention, that due to the extensive collection of foiled crystals available in the market in term of colors, sizes and shapes, the second method focuses on LED design that may enable seamless integration onto existing crystal design without spending effort and tools for customizing the crystals. Referring to FIG. 6 (a), FIG. 6 (b), and FIG. 6 (c) illustrates an illuminated transflective gemstone-LED combination, in accordance with an embodiment of the present invention and Referring to FIG. 7 (a), and FIG. 7 (b) are illustrated an illuminated transflective gemstone-LED combination, in accordance with an embodiment of the present invention.

FIG. 6 (a) 610 illustrates a gemstone with standard mirror coating known as "FOILED" and side lit LED in bezel setting; FIG. 6 (b) 612 illustrates an LED strip that can wrap around a gemstone edge for providing side lit LED; and FIG. 6 (c) 614 illustrates a foldable FPC for side lit LED and a "FOILED" gemstone. As shown in FIG. 6 (a) 610 the transflective gemstone-LED combination includes a foiled crystal 618 with an optional dichroic mirror coating 616, a bezel/cup chain 620, an LED Die 622 (side-lit in certain embodiments), an FPC 624, and a foiling i.e., an opaque mirror coating 626. In one embodiment, the LED is thin film FPC 624 LED/OLED 622 that is flexible enough to be positioned and conformed to the shape of gemstone/crystal and providing a side-lit LED die configuration to the crystal 618. As shown in FIG. 6 (b) 612, the thin film FPC LED/OLED may be a strip FPC 624 with the LED Die/package 622 that is capable of wrapping around the edge of the gemstone/crystal to provide a side-lit configuration. As shown in FIG. 6 (c) 614, the thin film FPC LED/OLED may be a foldable FPC 624 with the LED Die/package 622 that is capable of folding along the folding line 628 to form a folded FPC 632, wherein the folding line 628 marks the crystal location 630 of the gemstone/crystal to provide a foldable configuration. In one embodiment, the thin film LED described hereinabove may adapt to existing cup chain. In certain embodiments, the LED package may be removed to enable the LED to LED pitch since package LED may usually be large and may require surface mount spacing. Using the LED without the LED package may also assist in reducing the weight and improve bendability.

Figure 7:
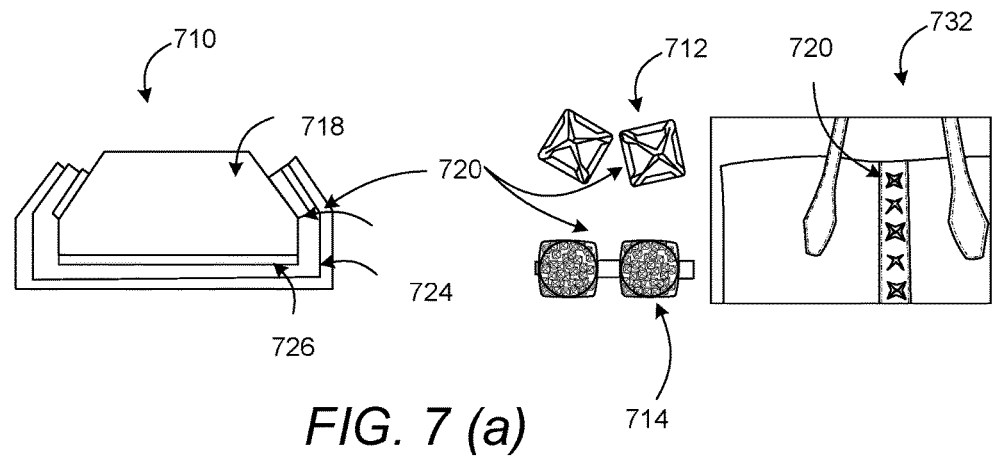
FIG. 7 (a) and FIG. 7 (b) illustrate an illuminated transflective gemstone-LED combination, in accordance with an embodiment of the present invention.
Figure 7:
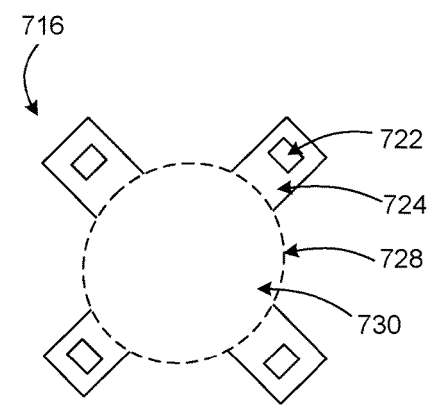

FIG. 7 (a) 710 that illustrates a "FOILED" gemstone with front lit LED with a photograph 712, 714 showing the prong supporting the LED FPC; and FIG. 7 (b) 716 that illustrates a foldable configuration for COF FPC for front lit LED. As shown in FIG. 7 (a) 710 the transflective gemstone-LED combination includes a foiled crystal 718, a leather substrate 720, a bezel/cup chain/prong shown in photographs 712, 714, an LED Die 722 (front-lit in certain embodiments), an FPC 724, and a foiling i.e., an opaque mirror coating 726. In one embodiment, the LED is thin film FPC 724 LED/OLED 722 that is flexible enough to be positioned and conformed to the shape of gemstone/crystal and providing a front-lit LED die configuration to the crystal 718. As shown in FIG. 7 (b) 716, the thin film FPC LED/OLED may be a foldable FPC 724 with the LED Die/package 622 that is capable of folding along the folding line 728, wherein the folding line 728 marks the round crystal location 730 of the gemstone/crystal to provide a foldable configuration. As shown in FIG. 7a 710, the thin film FPC LED/OLED may be hidden and structurally supported by the gemstone/crystal cup chain/prong 712, 714/bezel/settings (a metal piece that hold the crystals onto leather/fabric/chain) or a flexible material such as leather 732. The front lit LED may provide a not so glaring light due to reflected light and may have a good light effect of gemstone/crystal.

Figure 8:
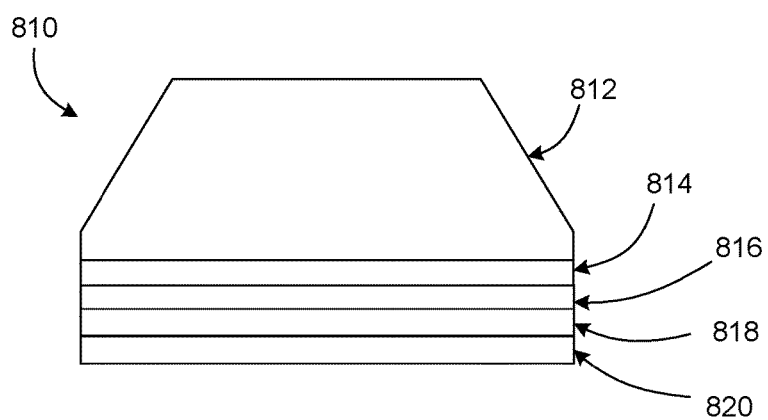
FIG. 8 illustrates a cross sectional view of an illuminated transflective gemstone-LED combination, in accordance with an embodiment of the present invention.

In another embodiment, the opaque mirror coating i.e., the non-transparent mirror coating is not on a gemstone/crystal but opaque mirror layer can be constructed of an OLED cathode, PCB and FPC material consisted of a rigid or flexible reflective metal layer, metalized film and the like. Referring to FIG. 8 is illustrated a cross sectional view of an illuminated transflective gemstone-LED combination, in accordance with an embodiment of the present invention. As shown in FIG. 8 800 the transflective gemstone-LED combination includes an unfoiled crystal 812, a clear adhesive 814, an OLED transparent substrate, for example glass 816, a transparent OLED anode 818, and a mirror OLED cathode 820. In the embodiment, shown in FIG. 8, the gemstone or crystal may be unfoiled 812 i.e., transparent and colored or transparent and colorless. In one embodiment, the LED i.e., the OLED 818 may be back-lit. In the embodiment, shown in FIG. 8, the opaque mirror coating 820, i.e., the mirror OLED cathode may be positioned at the back end behind the LED/OLED and gemstone/crystal. The embodiment, described in FIG. 8 may be advantageous in that there is no semi-transparent dichroic mirror which may filter the white LED light color. The illuminated transflective gemstone-LED combination provided in FIG. 8 may be employed for interior lighting or automotive headlight/rear light or automotive interior lighting or application which requires better LED color accuracy. In the embodiment, showing in FIG. 8, i.e., where OLED is employed as the LED the typical OLED layer system may consist of layers including the glass substrate 816 and OLED anode 818 which are both transparent, and the cathode 820 which may be made from a metal such as aluminum or silver. When the illuminated transflective gemstone-LED combination described with reference to FIG. 8 is switched-OFF, it may be perceived as a mirror. The OLED may be a single color or a multi-color OLED that may be a light source or matrix display. The OLED light may not scintillate or create sparkle like inorganic LED due to its more diffused and homogenous nature but it may be used to relay text, images and video. In one embodiment, the illuminated transflective gemstone-LED combination described in FIG. 8, may include multiple pieces of gemstone/crystals per OLED panel for lighting or display panel. For display panel, each crystal may be considered a unit pixel. In one embodiment, the OLED pixel may be the same size as the crystal if it is big enough to match. In another embodiment, the OLED may include multiple pixels consolidated to a single crystal. The mounting of crystal may be carried out using adhesive as mentioned hereinabove. In one embodiment, the OLED anode and cathode may be built on top of the gemstone itself superseding the flat glass substrate 816 as shown in FIG. 8 since the OLED is built on a flat glass substrate, which may assist in eliminating the use of the adhesive 814.

Figure 9:
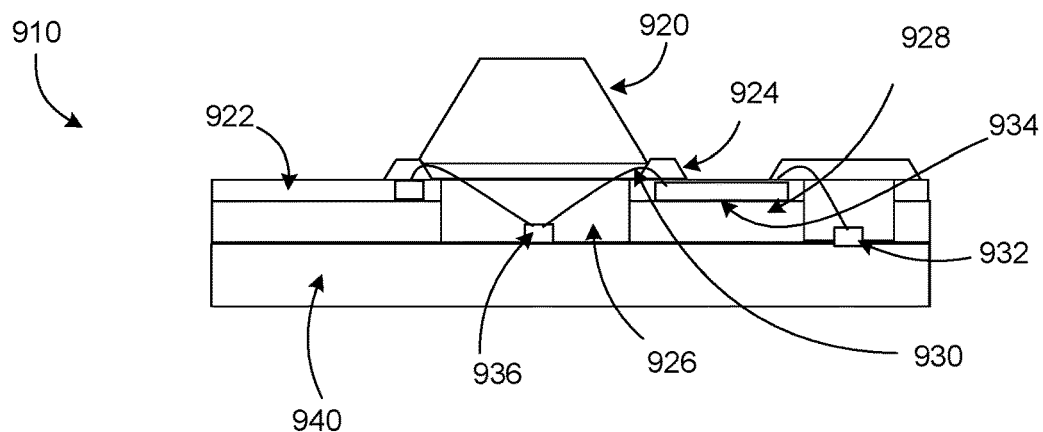
FIG. 9 (a), FIG. 9 (b), FIG. 9 (c), FIG. 9 (d), and FIG. 9 (e) illustrate an illuminated transflective gemstone-LED combination, in accordance with an embodiment of the present invention, wherein FIG. 9 (a) illustrates an unfoiled Gemstone with mirror coated substrate on LED COB/COF using lateral LED chip and wire bond, FIG. 9 (b) illustrates a bare mirror coated COB/COF substrate, FIG. 9 (c) illustrates an unfoiled crystal mounted on COB substrate that enables the same result as a "FOILED" gemstone, FIG. 9 (d) illustrates an unfoiled gemstone with mirror coated substrate on LED COB/COF using flip-chip/thin film flip chip LED chip, FIG. 9 (e) illustrates an unfoiled gemstone with plated mirror on two copper layers COB/COF substrate on using flip-chip/thin film flip chip LED chip.
Figure 9:
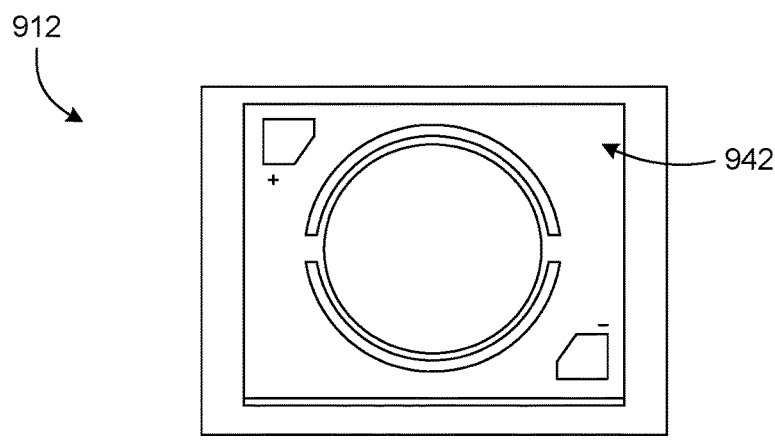
Figure 9:
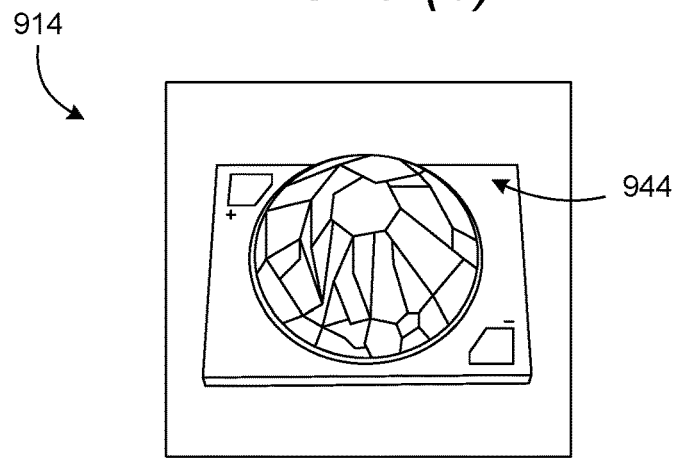
Figure 9:
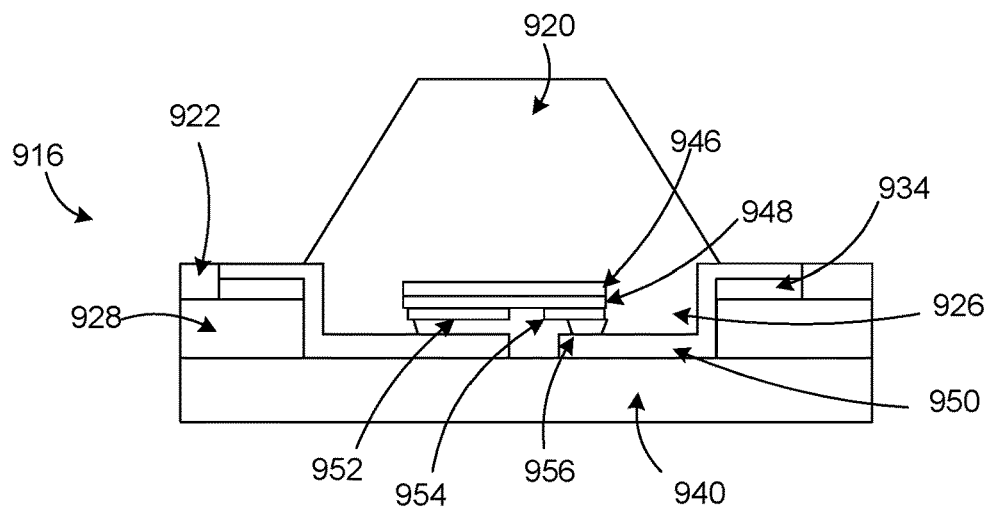
Figure 9:
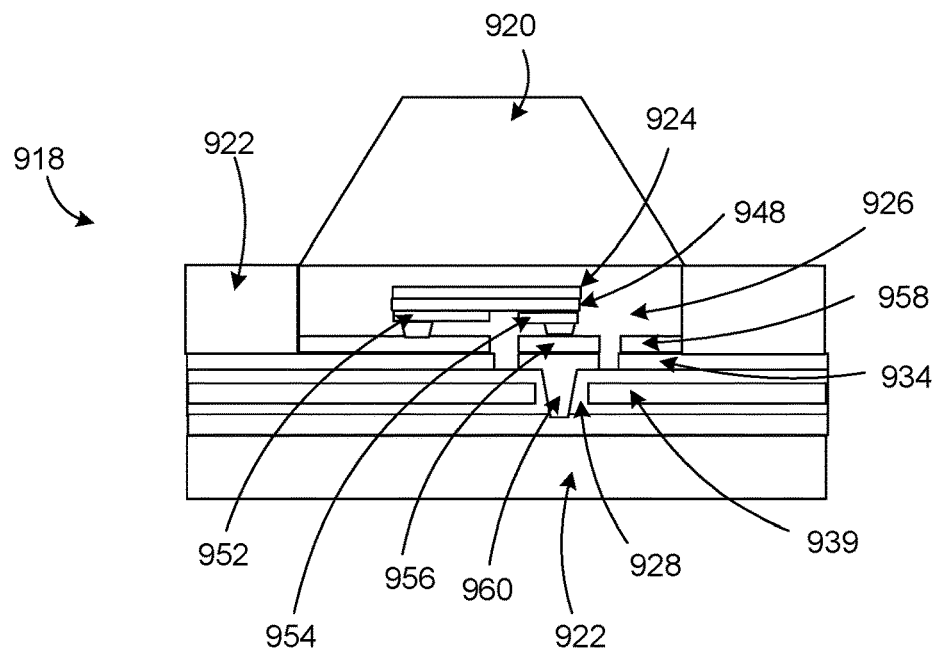

FIG. 9 (a), FIG. 9 (b), FIG. 9 (c), FIG. 9 (d), and FIG. 9 (e) illustrates an illuminated transflective gemstone-LED combination, in accordance with an embodiment of the present invention. FIG. 9 (a) 910 illustrates an unfoiled gemstone with mirror coated substrate on LED COB/COF using lateral LED chip and wire bond; FIG. 9 (b) 912 illustrates a bare mirror coated COB/COF substrate; FIG. 9 (c) 914 illustrates an unfoiled crystal mounted on COB substrate that enables the same result as a "FOILED" gemstone; FIG. 9 (d) 916 illustrates an unfoiled gemstone with mirror coated substrate on LED COB/COF using flip-chip/thin film flip chip LED chip; and FIG. 9 (e) 918 illustrates an unfoiled gemstone with plated mirror on two copper layers COB/COF substrate on using flip-chip/thin film flip chip LED chip.

As shown in FIG. 9 (a) 910 the transflective gemstone-LED combination includes a unfoiled crystal 920, a coverlay 922, an optional dam ring 924, a clear silicone encapsulant with adhesive property 926, a dielectric layer 928, a wire bond 930, an LED driver die 932 (placed on the edge in this embodiment), a copper layer 934, a LED die 936, and a mirror finish metal 940. In the embodiment, described in FIG. 9, the LED die 936 may include but is not limited to LED made with COB (chip on board), COF (chip on flex)/FCOF (flip chip on flex), COG (chip on glass) method; a substrate 940 may include an opaque mirror layer, i.e., a metal layer made of high reflective aluminum/mirror finish aluminum plate, a metal layer made of copper clad vacuum coated or electroplated with silver/aluminum or other suitable metals to give the mirror effect. In the embodiment, provided in FIG. 9 (a) 910 the reflector for both the gemstone mirror foiling and the LED artificial light reflector may be consolidated by using the substrate 940. It may be appreciated by a person with ordinary skill in the art, in light of and in accordance with the teachings of the present invention, that the substrate 940 i.e., the mirror finish metal layer is heat conductive and assists in dissipating the heat from the LED die 936 and the LED driver 932. The mirror finish metal layer 940 may also be electrically conductive as a power or a ground plane. FIG. 9 (b) illustrates the mirror substrate that may be used in embodiments shown in FIG. 9 (a) and FIG. 9(d). Accordingly, as shown in FIG. 9b 912 the substrate may include but not be limited to, a bare mirror coated COB/COF substrate 942, a metal core PCB or AT&S's (Austria Technologie & Systemtechnik Aktiengesellschaft) insulated metallic substrate PCB using highly reflective aluminum mirror like the mirror finish metal 940. FIG. 9 (c) illustrates a gemstone mounted onto the mirror substrate but without any internal circuitry. Accordingly, FIG. 9 (c) 914 illustrates an unfoiled crystal mounted on COB substrate 944 that enables the same result as a "FOILED" gemstone. In one embodiment, the dam ring 924 may be white silicone material dispensed and heat cured to function as a side reflector and a housing for the gemstone 920. In one embodiment, the clear silicone encapsulant 926 may have adhesive property to glue the gemstone 920. In one embodiment, in the COB substrate, the dielectric layer 928 may be rigid and may be made of ceramic material. Two cavities may be formed to mount lateral LED die 936 and LED driver 932 separately. It may be appreciated by a person with ordinary skill in the art, in light of and in accordance with the teachings of the present invention, that LEDs may include but is not limited to a lateral LED, a flip-chip LED/thin-film flip-chip LED, and a vertical LED. In one embodiment, the LED employed in FIG. 9 may include a transparent LED display, i.e., an array of the same dies forming a LED display, which is essentially also a COB method using microscopic LED dies diced from wafer without a package. It may be appreciated by a person with ordinary skill in the art, in light of and in accordance with the teachings of the present invention, that typically the LED driver 932 may be larger in size than the LED die 936 and may be visible to human eyes when viewed at a very short distance. Accordingly, the LED driver 932 may be placed in a second cavity away from the gemstone and encapsulated with white silicone as shown in FIG. 9 (*a*). In one embodiment, the LED driver 932 may be placed on the bottom layer of a dual copper layer PCB/FPC (not shown in figure). The LED/LED driver may be connected to circuitry via wire bond, flip chip for COB, and COF/FCOF. In certain embodiments, wire bond for micro-LED may be used as it may be near invisible to human eyes. In embodiments where the wire bond is considered visible to human eyes, flip chip LED may be employed.

As shown in FIG. 9 (*d*) 916, the transflective gemstone-LED combination includes an unfoiled crystal 920, a coverlay 922, an LED substrate 946, a flip Chip LED 948, a copper layer 934, a clear silicone encapsulant with adhesive property 926, a transparent conductive layer 950, a mirror finish metal 940, a dielectric layer 928, p-type contact 952, a N-type contact 954, and a bump 956. Accordingly, FIG. 9 (*d*) 916 is an embodiment where a flip chip LED 948 and a transparent conductive layer 950 may be used as replacement for the lateral LED 936 and the wire bond 930 used in FIG. 9 (*a*) 910. In one embodiment, the transparent conductive layer 950 may include a transparent conductive oxide such as ITO deposited by vapor deposition sputtering. In another embodiment, the transparent conductive layer 950 may be printed with transparent conductive ink such as carbon nanotube, graphene or sintered silver nano-wire mesh or ITO. In one embodiment, the electrical contact between the LED pad 952 and 954 of the flip chip LED 948 and the transparent conductive layer 950 may be realized via cold welding of metallic micro-contacts i.e., gold stud bump 956 or by using a conductive bond (printable, UV curable adhesive containing silver nanoparticles).

As shown in FIG. 9 (*e*) 918, the transflective gemstone-LED combination includes an unfoiled crystal 920, a coverlay 922, an LED substrate 946, a flip Chip LED 948, a copper layer 934, a clear silicone encapsulant with adhesive property 926, a plated mirror 958, a non-reflective metal core 939, a dielectric layer 928, p-type contact 952, a N-type contact 954, a bump 956, a via 962 and the coverlay 922. Accordingly, FIG. 9 (*e*) 918 is an embodiment, wherein a flip chip LED 948 uses two conductive copper layers 934, 935 PCB/FPC and a via 960 connected an island on top copper layer 934 to bottom copper layer 935. In one embodiment, the plated mirror 958, i.e., the opaque mirror layer may be formed using electroless plating/electro-plate with silver over the top copper layer 9344. The mirror layer may be electrically conductive and typically having an area as large as the gemstone 920 back surface. In embodiments, where an RGB LEDs configuration is employed, the mirror layer may be common anode/cathode for power/ground contact respectively. FIG. 9 (*e*) 918 may also include an anode mirror layer, for example, connecting the p-type contact 952 of the LED 948 and an n-type contact 950 that may have a small mirror island in the mirror layer. The small mirror island is the mirror plated top copper layer 934 having a via 960 connected to the bottom copper layer 935. One P/N contact may be chosen to be a small mirror island such that it may not create two huge separate mirror planes that may not be aesthetic. In one embodiment, the spacing between the anode and the cathode mirrors may be in a range of about 50 micrometers such that the mirror layer may seem as a full mirror like the gemstone foiling. The N-type contact 954 may be connected to the bottom copper layer 935 through a via 960. In one embodiment, the optional none-reflective metal core 939 may include but not be limited to an aluminum layer used for heat dissipation or a metal layer that is embedded and is capable of being bent into gemstone metal settings. In some embodiments, the COF LED in FIGS. 9 (*d*) 916 and 9 (*e*) 918, may employ thin film flip chip LED where the LED substrate 924 is removed by laser lift off. It may be appreciated by a person with ordinary skill in the art, in light of and in accordance with the teachings of the present invention, that the laser lift off process which removes the LED substrate is a common process for TFFC LED. Removing the substrates may improve light extraction and hence improve efficiency and flip chip improves heat dissipation In some embodiments, the COF LED in FIGS. 9 (*a*) 910 and 9 (*d*) 916, the flexible circuit material 940 i.e., the COF substrate is a copper-aluminum composite FPC, for example, Multek's Q-Prime where the aluminum i.e., the metal core 940 is customized/polished to be highly reflective and flexible at a thickens of about 0.1 millimeter and may be suitable for roll-to-roll processing. In another embodiment, the substrate for COF LED may include an aluminum layer 940 made of aluminum metallized polyimide film where the aluminum may have a thickness in a range of about 0.2 micrometers to about 0.5 micrometers, or may include another copper layer electroplated or vacuum coated with mirror silver/aluminum. In one embodiment, the dielectric layer 928 may include a flexible polyimide.

In one embodiment, for COB, the metal substrate may be rigid; for COF, the metal substrate may be a thin metal foil that is flexible. In certain embodiments, the COF metal substrate may be made thicker for a one-time flex, such that the substrate may be bent into a prong or a metal settings for the gemstone. In order to realize individual discrete LED similar to SMD LED, the COB/COF LED can be singulated into individual LED like SMD LED by die cutting from a MCPCB panel and by die cutting or laser cutting FPC roll or sheet. In one embodiment, the substrate may include a double copper layer MCPCB or FPC. In certain embodiments, the LED used may include but no limited to inorganic white LED of GaN based blue LED with yellow phosphorus in chip scale package or wafer level package where the yellow phosphorus may be visible at a micro-level, and ZnSe based white LED.

Figure 10:
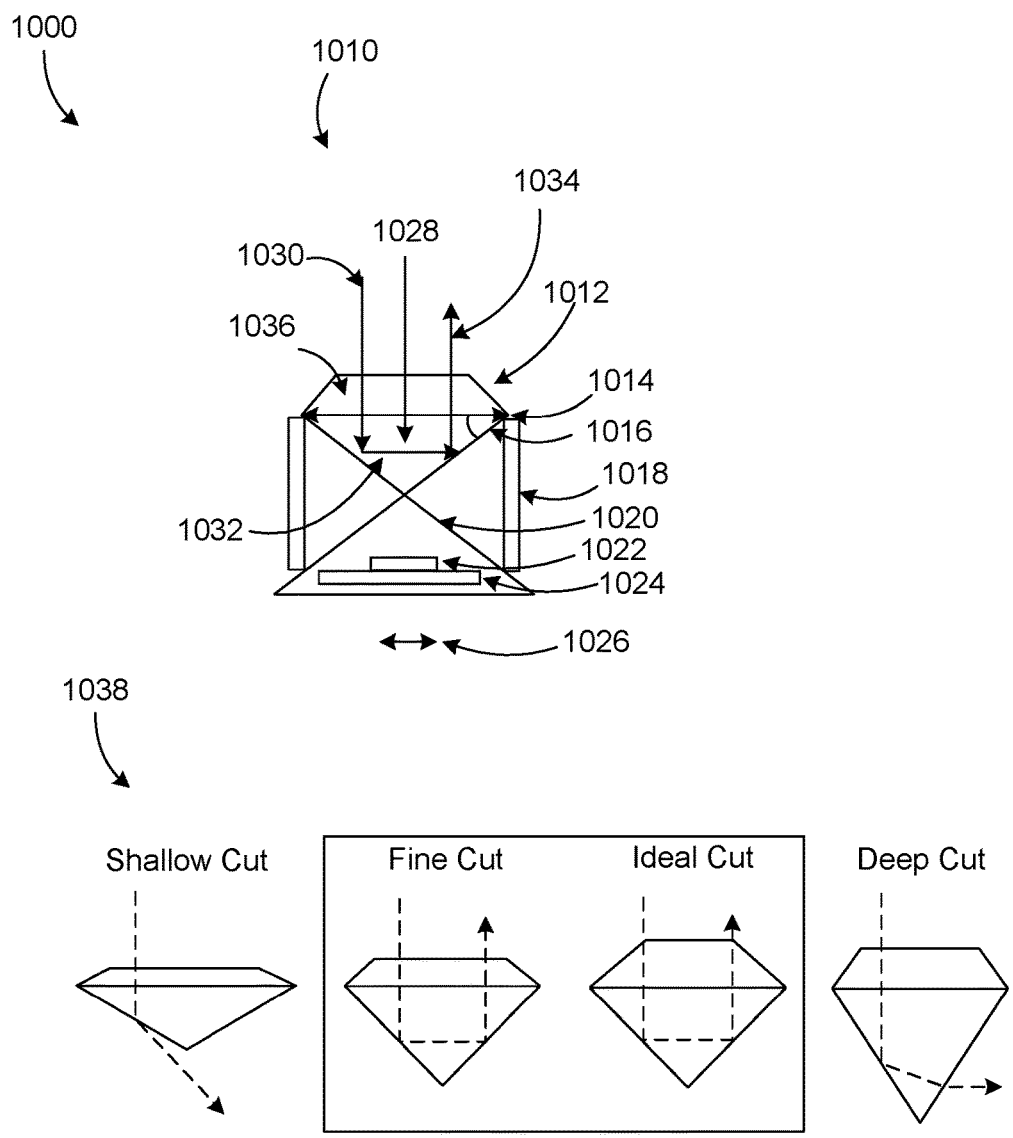
FIG. 10 illustrates an illuminated transflective gemstone-LED combination, in accordance with an embodiment of the present invention.

Referring to FIG. 10 is illustrated an illuminated transflective gemstone-LED combination 1000, in accordance with an embodiment of the present invention. As shown in FIG. 10 view 1010 the illuminated transflective gemstone-LED combination may include a pointed back gemstone without the "FOILED" coating able to reflect light and conceal LED visibility, according to an embodiment of the present invention. The illuminated transflective gemstone-LED combination shown in view 1010 may include an unfoiled pointed back crystal 1012, a gem mount 1018, an LED die 1022, and a flex circuit 1024. Accordingly, the third method of mirror coating is described with reference to FIG. 10. In the illuminated transflective gemstone-LED combination 1010 of FIG. 10, the gemstones or the imitated gemstones i.e., crystal may be totally unfoiled, i.e., without mirror foiling or effect. The transflector may be based on the geometry/cutting/facets of the transparent clear/colored gemstones which may be pointed back i.e., the 1012 unfoiled pointed back crystal. It may be appreciated by a person with ordinary skill in the art, in light of and in accordance with the teachings of the present invention, that the pointed back crystal is actually a retroreflector that reflects ambient light back to its source. It may be appreciated by a person with ordinary skill in the art, in light of and in accordance with the teachings of the present invention, that diamond brilliance cut may give maximum reflection which flat back crystal structure may be unable to achieve. It is well known that a ray of light reflects totally off of a facet if its angle of incidence is higher than the critical angle. A light ray travelling vertically downward through a table surface of gemstone (gemology term) will reflect if the pavilion facet angle is above the critical angle. Hence, it may be preferred that the pavilion angle is greater than the gemstone material critical angle. For example, critical angle for crown glass to air boundary is 41 degree and diamond-air boundary is 24 degrees; hence each cut glass crystal and diamond needs to have pavilion angle greater than its own critical angle. In one embodiment, when viewed from the viewing angle 1 1028, the light reflection path passing through path 1030, 1032, 1034 may prevent a viewer from seeing through and observing what is behind the crystal thus enabling the concealment of a yellow phosphorus coated white LED 1022 having a diameter 1026 and the LED circuitry. However, when the observation angle is increased to viewing angle 2 1036, the reflector performance of the crystal may be weakened. LED die placed on a pointed back crystal in a similar fashion as FIG. 5 will become visible at viewing angle 2 1036. Accordingly, as shown in FIG. 10 a gemstone mount/metal setting 1018 and a blind spot zone 1020 for LED positioning are suggested. The blind spot is where the LED may be positioned such that it is invisible during light off mode at all viewing angle from the crown of the gemstone. In one embodiment, the gemstone mount may include a reflective metal inside such that while viewing at zero-degree angle of incidence to the crown or bezel facet, the gemstone may show the reflective mount. The blind spot zone 1020 may be considered as an imaginary cone structure or inverted brilliant cut gemstone volume at the pointed tip/cutlet (cutlet is used to refer to the tip of gemstone even for no cutlet gemstone as in FIG. 10) of the pavilion. In one embodiment, the cone structure i.e., the blind spot zone 1020 may have a slop angle same as the pavilion angle 1016. In one embodiment, the LED/yellow phosphorus area 1022 may be smaller than the diameter of the girdle 1014 of the gemstone 1012 and preferably as small as possible to stay within the imaginary cone structure along the vertical axis of the gemstone. In one embodiment, the LED die 1022 (back-lit in certain embodiments) may include any small LED preferably chip scale package yellow phosphorus white LED or RGB LED. It may be appreciated by a person with ordinary skill in the art, in light of and in accordance with the teachings of the present invention, that the further the LED position behind the pavilion of the gemstone, the better it is concealed from the view. The light reflection may be constantly seen from many angles of view point of the crystal especially from the table surface (gemology term) and in many ways prevent one from seeing through what is behind the crystal. In the embodiment described in FIG. 10 the pointed back gemstone may allow the LED light to shine from the back of the crystal. The pointed back gemstone consists of multiple pavilion facets and/or lower girdle facets in various cut including but not limited to point cut, table cut, old single cut, Mazarin cut, Peruzzi cut, old European cut and round brilliant cut that those skills in art are familiar with.

In one embodiment, is provided a fourth method of mirror design wherein the transflector may include a switchable mirror i.e., a reversible electrochemical mirror, operating in two states, that is in mirror state when power is switched-OFF and in transparent state when power is switched-ON. It may be appreciated by a person with ordinary skill in the art, in light of and in accordance with the teachings of the present invention, that when voltage is applied so that the hydrogen ions move toward the switchable mirror layer, the transported ions react with the switchable mirror layer, forming a metal hydride. Since the metal hydride is transparent, the device changes from the mirror state to the transparent state. This change may be reversible. When voltage of the opposite polarity is applied, the hydrogen ions move out of the metal hydride in the switchable mirror layer and the layer returns to the original metal, returning the device to the mirror state. In one embodiment, the construction may be similar to the construction shown in FIG. 4, with the electrochemical mirror transflector replacing the one-way mirror coating on a transparent film 412 and sandwiched between the unfoiled gemstone 410 and the LED die 414. FIG. 10 also illustrates gemstones 1038 with different cuts including but not limited to, shallow cut, fine cut, ideal cut, and deep cut.

Figure 11:
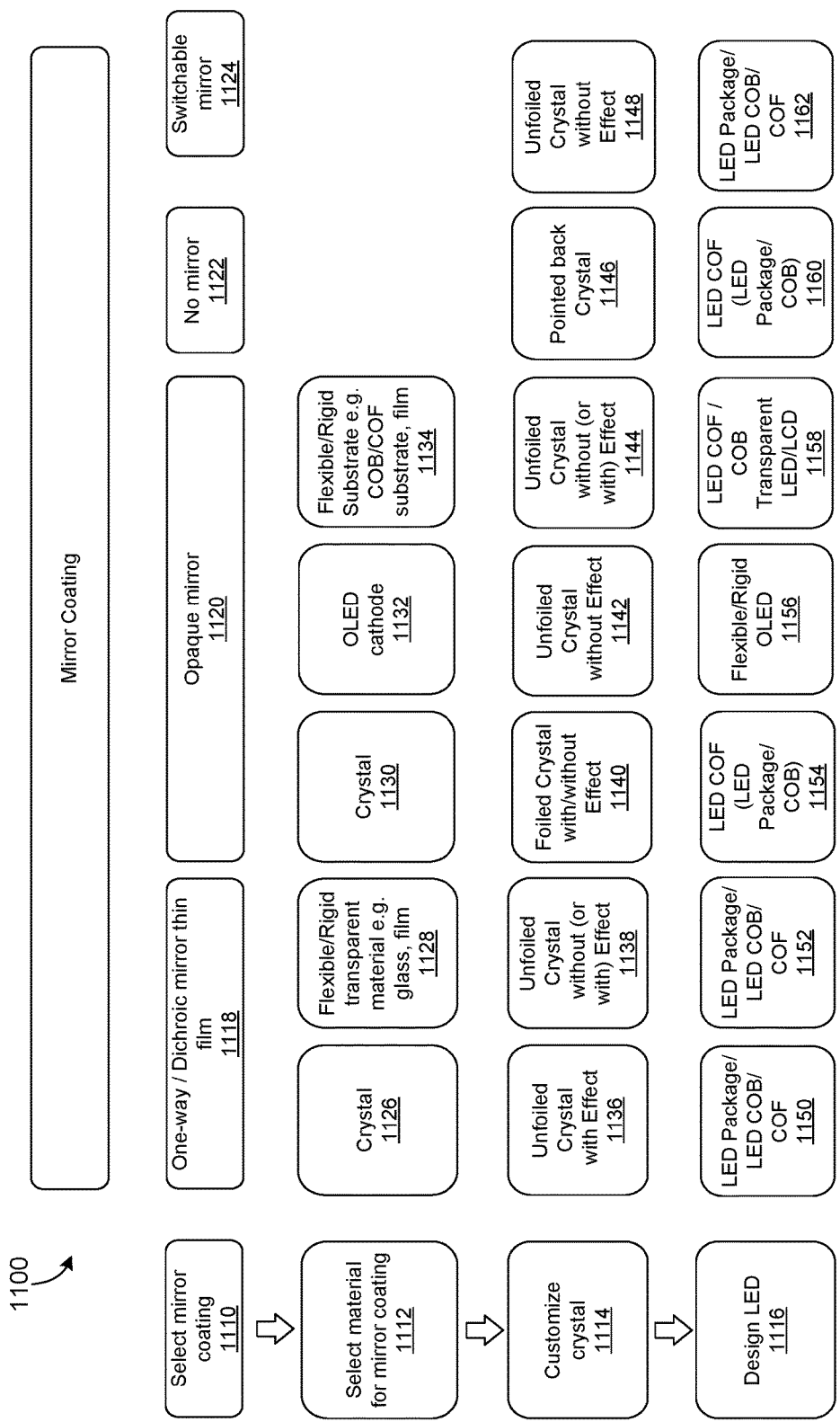
FIG. 11 illustrates an exemplary flowchart for a method of fabricating an illuminated transflective gemstone-LED combination, according to an embodiment of the present invention.

Referring to FIG. 11 is illustrated an exemplary flowchart for a method of fabricating illuminated transflective gemstone and LED combination, according to an embodiment of the present invention. In a first step 1110 a mirror coating may be selected from one of the four methods described herein, i.e., one-way/dichroic mirror thin film 1118, opaque mirror 1120, no mirror 1122, and switchable mirrors 1124. In a second step 1112, a substrate may be selected for using the coating selected in step 1110. In various embodiments, the substrate for the one-way mirror thing film 1118 may include a crystal 1126, a flexible/rigid transparent material like glass or film 1128; the substrate for an opaque mirror coating 1120 may include a crystal 1130, an OLED cathode 1132, a flexible/rigid substrate e.g., COB/COF substrate, film; and no substrate may be needed for no mirror 1122 and the switchable mirror 1124. In a third step 1114 the crystal selected in step 1112 may be customized. In one embodiment, the crystal 1126 may be customized as an unfoiled crystal with effect 1136, the flexible/rigid transparent material 1128 may be customized as an unfoiled crystal with or without effect 1138, the crystal 1130 may be customized as a foiled crystal with or without effect 1140, the OLED cathode 1132 may be customized as an unfoiled crystal without effect 1143, the flexible/rigid substrate 1134 may be customized as an unfoiled crystal with without effect 1144, a pointed back crystal 1146 may be used for the no mirror crystal selection 1122, and an unfoiled crystal without effect 1146 customization may be provided for the switchable mirror crystal selection 1124. In a fourth step 1116, the LED may be designed as a LED package/LED COB/COF 1150, 1152 for the one-way/dichroic mirror thin film 1118 selection, LED COF/LED Package/COB 1154 or Flexible/Rigid OLED 1156 or LED COF/COB transparent LED/LCD 1158 for the opaque mirror 1120 selection, LED COF/LED Package/COB 1160 for the no mirror selection 1122, and LED Package/COF/LED COB 1162 for the switchable mirror 1124 selection. Accordingly, the method of fabricating illuminated gemstone and LED according to an embodiment of the present invention may include a first step where the mirror coating type is selected, a second step where the material is selected for mirror coating, a third step where the crystal is customized, and fourth step where a plurality of LED design is selected based on various product requirement.

In one embodiment, a number of illuminated transflective gemstone and LED combination i.e., gemstone-LEDs, may be connected together in various shapes, sizes, as rigid/flexible substrate to form a line, circular ring or matrix, and may be made into a display for smart clothing, shoes, bags, jewelry, bracelet, timepiece, luminous wall paper, lighting and the like. In one embodiment, the light may show a notification, time, text, images and video. In one embodiment, the LED light may not be limited only to machine to human communication but nay also be used for machine to machine such as infrared or LIFT (light fidelity). In one embodiment, the LED may be triggered by motion to show images/video with persistence of vision. Accordingly, the gemstone-LEDs described herein may be applied to costumes for dance or sport like gymnastics, figure skating and the like. It may be appreciated by a person with ordinary skill in the art, in light of and in accordance with the teachings of the present invention, that various sensors such as accelerometer, gyroscope, magnetometer, temperature sensor, pressure sensor, skin galvanic sensor, touch sensor, microphone, and camera may be used to control the LEDs. The LEDs can also be wirelessly control via Bluetooth, Wi-Fi, ZigBee, and etc. These controllers may be in different section of the system either on PCB or FPC or it can be embedded/mounted on the bottom layer of the FPC of LED. If the controller is in unpackaged die on FPC, the gemstone acts as rigid body to protect mechanical support.

In various embodiments, the gemstone LEDs disclosed herein may have various purposes including but not limited to enabling aesthetic LED cover look with a huge available collection of existing gemstone color, shape and size; enabling gemstones to have digital control sparkle and convey info, message, text, image, and video; the ability to conceal LED light source to preserve the aesthetic appearance of gemstones during close up view; the ability to integrate and adapt various LEDs onto various cuts, facets and shapes of gemstones in very compact rigid or flexible substrates or systems; the ability to enable multiple controllable LED lighting directions and positions mimicking surrounding ambient light, and the like purposes.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing designs for gemstone-LEDs, and methods, and apparatus for making the gemstone-LEDs according to the present invention will be apparent to those skilled in the art. Various aspects of the invention have been described above by way of illustration, and the specific embodiments disclosed are not intended to limit the invention to the particular forms disclosed. The particular implementation of the designs for gemstone-LEDs, and methods, and apparatus for making the gemstone-LEDs may vary depending upon the particular context or application. By way of example, and not limitation, the designs for gemstone-LEDs, and methods, and apparatus for making the gemstone-LEDs described in the foregoing were principally directed to aesthetic use of the gemstone-LEDs implementations; however, similar techniques may instead be applied to LED digital signage/display, portable light, interior light, automobile lighting, architectural lighting, consumer electronic LED indicator, LED of computing, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

What is claimed is:

1. An apparatus comprising:
   a gemstone, said gemstone comprises at least one of synthetic gemstone, imitated gemstone, precious stones, semi-precious stones, and cut glass crystals;
   an optical or transflector coating implement, said optical coating or transflector implement comprises at least one of a one-way mirror coating material and a dichroic mirror coating material, wherein said optical or transflector coating implement is configured to provide at least one of a one-way mirror and iridescent dichroic mirror;
   wherein said optical or transflector coating implement is provided on a proximate back surface area of said gemstone;
   a substrate, wherein said substrate is coated with said optical or transflector coating implement, wherein said optical or transflector coating implement is configured to result in a metallic mirror and/or iridescent effect on said substrate;
   a light source, said light source comprises a light emitting diode (LED) die having an internal circuitry, wherein said light source is configured to be operable for illuminating said gemstone, and wherein when said light source is in a switched-Off mode, said metallic mirror effect or said iridescent effect is configured to conceal said internal circuitry of said light emitting diode (LED) die to provide an aesthetic look and color on said gemstone, and wherein when said light source is in a switched-ON mode said optical coating implement is configured to allows said light source to transmit through said substrate;
   wherein said optical or transflector coating implement is disposed between said light source and said back surface area of said gemstone;
   wherein said light source comprises a substantially invisible light source integrated onto said substrate.

2. The apparatus of claim 1, wherein said substrate comprises a transparent substrate comprising: a silicone encapsulant with adhesive properties, a flexible printed circuit board (FPC) that is configured to surface mount (SMT) said LED die with said silicone encapsulant, and a coverlay that is configured to cover, encase, and protect said LED die.

3. The apparatus of claim 2, wherein said gemstone is mounted into a cavity of said LED die with said silicone encapsulant injected into said LED die cavity.

4. The apparatus of claim 1, wherein said substrate is rigid or flexible, and wherein said dichroic mirror coating material is provided on a proximate front surface portion of said gemstone.

5. The apparatus of claim 1, wherein said one-way mirror coating material is disposed on said back surface portion of said gemstone, and wherein said one-way mirror coating material has a broad band light reflection.

6. The apparatus of claim 1, wherein said optical or transflector coating implement further comprises at least one of a trichroic, and a pleochroic mirror coating material.

7. The apparatus of claim 6, wherein a coating process carried out with said optical or transflector coating implement comprises at least one of vacuum sputtering, vapor coating (physical vapor deposition or chemical vapor deposition), and spray coating process.

8. The apparatus of claim 1, wherein said light source further comprises a controllable LED package that is configured to operate in ambient light reflective mode and LED light transmissive mode.

9. The apparatus of claim 1, wherein said light source is configured to be controlled by at least one of a central processing unit (CPU), a microcontroller, and a LED driver.

10. The apparatus of claim 1, further comprising:
    a COF LED, wherein said COF LED is configured to adapts to various cuts, facets and shapes of gemstones in rigid or flexible substrates or systems, said COF LED is further configured to enable multiple controllable LED lighting directions including front lit, side lit and back lit configurations over said gemstones; and wherein said LED lighting directions are configured to hide/mask said COF LED from visibility when positioned in said front lit and side lit configurations.

11. The apparatus of claim 10, further comprising a gemstone supporting structure, wherein said gemstone supporting structure comprise a prong or metal settings integrated with said COF LED.

12. The apparatus of claim 10, further comprising a silicon die, wherein said silicon die is configured to reduce a weight and size of said apparatus, and wherein said light source has flexibility and a stretchable structure.

13. The apparatus of claim 1, in which said gemstone implement comprises a pointed back crystal material, wherein said crystal material has a pavilion angle greater than a critical angle of said crystal material and an equally or less denser medium behind said pointed back crystal, and wherein said crystal material is configured to forms a retroflector resulting in a blind spot;
   wherein said blind spot is configured to conceal said LED internal circuitry from all viewing angles from a crown of said gemstone implement;
   wherein said LED light source comprises a yellow phosphorus white LED;
   wherein there is substantially less distortion of white light color;
   wherein said crystal material is transparent with reflectivity; and
   wherein said LED light source has a wide size tolerance for gemstones having a variety of sizes.

14. The apparatus of claim 1, further comprising:
   a transflector layer, wherein said transflector layer comprises a switchable mirror coating, wherein said switchable mirror is an electrochemical mirror having a mirror state in a switched-OFF mode and having a transparent state in a switched-ON mode, and wherein said switchable mirror layer further comprises a metal hydride that is configured to change from said mirror state to said transparent state, and from said transparent state to said mirror state; and
   wherein said gemstone implement comprises an unfoiled crystal;
   wherein said transflector layer is disposed proximately between said LED and said gemstone implement.

15. An apparatus consisting of:
   a gemstone implement, said gemstone implement comprises at least one of synthetic gemstone, imitated gemstone, precious stones, semi-precious stones, and cut glass crystals;
   a coating implement, said coating implement comprises at least a mirror coating material;
   an organic light emitting diode (OLED) having an anode and a cathode, wherein said organic light emitting diode (OLED) is configured to be operable as a light source;
   wherein said mirror coating material is disposed on a surface proximately behind said organic light emitting diode (OLED) cathode;
   wherein said OLED anode is generally transparent when said light source is switched-ON and luminous when said light source is switched-OFF;
   wherein said OLED cathode comprises an aluminum or silver metal material;
   wherein said OLED cathode is configured to be reflective and provides ambient light reflection and OLED artificial light reflection;
   a transparent substrate,
   wherein there is no light color filtering since light from the OLED transmits through said transparent substrate and said gemstone implement to achieve better white light color accuracy;
   a transparent adhesive;
   wherein said gemstone implement is attached to said OLED via said transparent adhesive;
   wherein said transparent substrate is rigid or flexible.

16. The apparatus of claim 2, wherein said transparent substrate comprises glass or a gemstone.

17. An apparatus consisting of:
   a gemstone, wherein said gemstone comprises a square, triangular, or square shaped synthetic gemstone, imitated gemstone, precious stones, semi-precious stones, or cut glass crystals,
   a flexible printed circuit board (FCP), wherein said FPC is configured to conform to at least one of said square, triangular, and square shaped gemstone shapes;
   an opaque mirror coating material, wherein said opaque mirror coating material is disposed between said gemstone and said FPC;
   an LED package, said LED package comprises at least one of, a thin film flexible inorganic LED, a transparent display LEI)/LCD, and a mirror OLED lighting/display;
   wherein said thin film flexible inorganic LED is made with chip-on-board/chip-on-flex/flip chip-on-flex manufacturing technology, said transparent display LED/LCD is made with chip-on-board/chip-on-glass technology, and said mirror OLED lighting/display is configured to be flexible, bendable and conformal;
   wherein said LED package is embedded onto said FPC;
   wherein said opaque mirror coating material is configured to functions as a reflector;
   wherein said opaque mirror coating material is further configured to functions as a gemstone foil for ambient light reflection;
   wherein said LED package is layered on a proximate top portion of said opaque mirror coating material; and
   wherein said gemstone is transparent, colorless, white or colored.

18. The apparatus of claim 1, wherein said LED die and internal circuitry are substantially transparent.

19. The apparatus of claim 1, wherein said substrate is configured to be operable for a roll to roll process, yet rigid to hold shape when bent and wherein said substrate is configured to be used as prong or metal settings for said gemstone.

* * * * *